(12) United States Patent
Shank

(10) Patent No.: US 8,597,366 B2
(45) Date of Patent: Dec. 3, 2013

(54) ANTI-REFLUX STENT

(75) Inventor: Peter J. Shank, Boylston, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1289 days.

(21) Appl. No.: 11/619,585

(22) Filed: Jan. 3, 2007

(65) Prior Publication Data

US 2007/0112437 A1 May 17, 2007

Related U.S. Application Data

(62) Division of application No. 10/302,781, filed on Nov. 21, 2002, now abandoned.

(51) Int. Cl.
*A61F 2/04* (2013.01)

(52) U.S. Cl.
USPC ........................ 623/23.68; 623/23.7

(58) Field of Classification Search
CPC ............... A61F 2/04; A61F 2/06; A61M 5/00
USPC ............. 623/23.7, 23.68, 1.24; 604/8–9
See application file for complete search history.

(56) References Cited

U.S. PATENT DOCUMENTS

| | | | |
|---|---|---|---|
| 4,655,771 A | 4/1987 | Wallstén | |
| 4,846,836 A * | 7/1989 | Reich | 623/23.68 |
| 4,850,999 A | 7/1989 | Planck | |
| 4,857,069 A | 8/1989 | Kira | |
| 4,954,126 A | 9/1990 | Wallstén | |
| 5,123,917 A | 6/1992 | Lee | |
| 5,314,473 A | 5/1994 | Godin | |
| 5,788,626 A | 8/1998 | Thompson | |
| 5,800,339 A * | 9/1998 | Salama | 600/29 |
| 5,824,049 A | 10/1998 | Ragheb | |
| 5,840,081 A * | 11/1998 | Andersen et al. | 623/1.11 |
| 5,861,036 A | 1/1999 | Godin | |

(Continued)

FOREIGN PATENT DOCUMENTS

| | | | | |
|---|---|---|---|---|
| CZ | 5985 | | 4/1997 | |
| GB | 2069339 A | * | 8/1981 | ............ A61M 25/00 |
| JP | 10211287 A | * | 8/1998 | ............ A61M 29/02 |
| WO | 0032137 | | 6/2000 | |

OTHER PUBLICATIONS

Mizumoto, Y., et al., "Trial Use of a Gore-Tex Covered Ultraflex Stent With Reflux Preventive Action for Cardioesophageal Cancer," Proceedings of Digestive Disease Week, Washington, D.C., May 10-16, 1997, p. A-424, Abstract 1688.

Mizumoto, Y., and K. Taekawa, "Application of GORE-TEX Covered Ultraflex Stent With Back Flow Prevention to Lower Esophageal Cancer," Gastroenterological Endoscopy 38 (Suppl. 2):1819, Aug. 1996, Abstract VW 3 (English translation of abstract).

Valbuena, J., "Endoscopic Palliative Treatment of Esophageal and Cardial Cancer: A New Antireflux Prosthesis," Cancer 53(4):993-998, Feb. 15, 1984.

(Continued)

*Primary Examiner* — Andrew Iwamaye
(74) *Attorney, Agent, or Firm* — Vidas, Arrett & Steinkraus, P.A.

(57) ABSTRACT

An anti-reflux stent includes an extended inner sleeve, a stent surrounding at least a portion of the inner sleeve and a coating that bonds the stent to the inner sleeve whereby the extended inner sleeve can have a cross-sectional thickness that varies along the length of the inner sleeve. The inner sleeve is made of a material having a thickness and/or flexibility such that the distal end not surrounded by the stent collapses under gastric pressure to prevent the contents of the stomach from flowing into an esophagus. Food and liquid can pass through an inner lumen of the inner sleeve to enter a stomach when desired.

10 Claims, 12 Drawing Sheets

(56) References Cited

U.S. PATENT DOCUMENTS

| | | | |
|---|---|---|---|
| 6,027,525 A * | 2/2000 | Suh et al. | 623/1.1 |
| 6,162,244 A * | 12/2000 | Braun et al. | 623/1.12 |
| 6,264,700 B1 * | 7/2001 | Kilcoyne et al. | 623/23.68 |
| 6,302,917 B1 * | 10/2001 | Dua et al. | 623/23.68 |
| 6,475,208 B2 * | 11/2002 | Mauch | 604/510 |
| 6,494,909 B2 | 12/2002 | Greenhalgh | |
| 6,764,518 B2 | 7/2004 | Godin | |
| 6,790,237 B2 * | 9/2004 | Stinson | 623/23.68 |
| 6,821,291 B2 * | 11/2004 | Bolea et al. | 623/1.11 |
| 2001/0020189 A1 * | 9/2001 | Taylor | 623/23.68 |
| 2002/0032487 A1 * | 3/2002 | Dua et al. | 623/23.68 |
| 2003/0040771 A1 * | 2/2003 | Hyodoh et al. | 606/200 |
| 2003/0149475 A1 * | 8/2003 | Hyodoh et al. | 623/1.19 |
| 2003/0212450 A1 | 11/2003 | Schlick | |
| 2004/0172141 A1 * | 9/2004 | Stack et al. | 623/23.65 |
| 2008/0033574 A1 * | 2/2008 | Bessler et al. | 623/23.68 |
| 2009/0099643 A1 * | 4/2009 | Hyodoh et al. | 623/1.15 |

OTHER PUBLICATIONS

Valbuena, J., "Endoscopic Palliative Treatment of Esophageal and Cardial Cancer: A Study of 40 Cases: A New Antireflux Prosthesis is Presented," Proceedings of the 13th International Cancer Congress, Seattle, Wash., Sep. 8-15, 1982, p. 695, Abstract 3980.

Valbuena, J., "Palliation of Gastroesophageal Carcinoma With Endoscopic Insertion of a New Antireflux Prosthesis," Gastrointestinal Endoscopy 30(4):241-243, Aug. 1984.

Valbuena, J., "Malignant Esophagopulmonary Fistula Treated by Fiberoptic Intubation of a Prosthesis," Gastrointestinal Endoscopy 31(4):281-283, 1985.

Valbuena, J.V., and H. Olarte, "Prótesis Peroral Endoscópica en el Tratamiento de Cáncer de Esófago y Cardias," Rev. Col. Gastroent. 2(1):17-22, Mar. 1987, with English translation entitled "Endoscopic Peroral Prosthesis in the Treatment of Esophageal and Cardial Cancer."

* cited by examiner

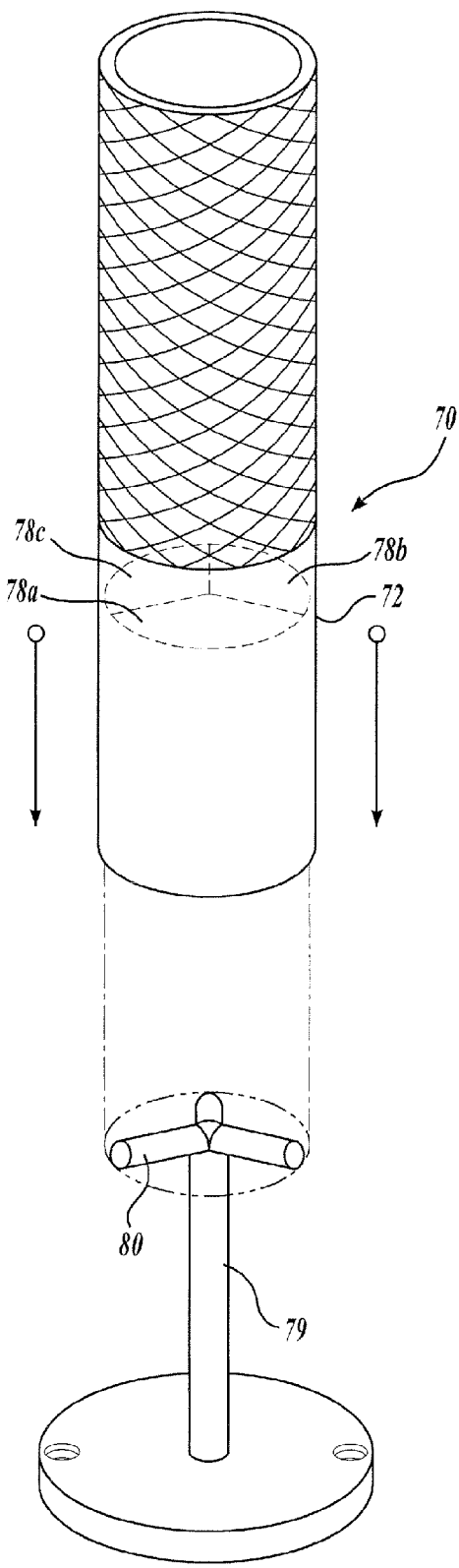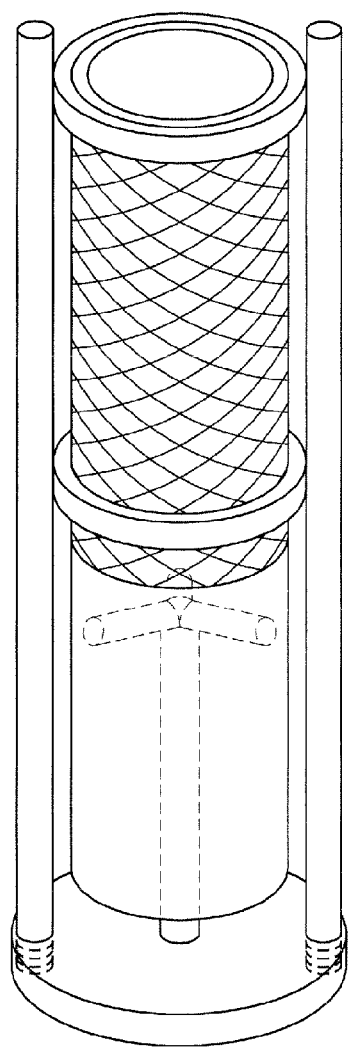
*Fig. 7A.* *Fig. 7B.*

US 8,597,366 B2

ANTI-REFLUX STENT

CROSS-REFERENCE TO RELATED APPLICATION

The present application is a divisional of U.S. patent application Ser. No. 10/302,781, filed Nov. 21, 2002, the benefit of which is hereby claimed under 35 U.S.C. §120 and which is fully incorporated by reference.

FIELD OF THE INVENTION

The present invention relates to medical devices in general, and to anti-reflux stents in particular.

BACKGROUND OF THE INVENTION

Gastroesophageal reflux disease (GERD) is a medical condition whereby stomach acids repeatedly enter the lower portion of the esophagus because the lower esophageal sphincter (LES) at the entrance of the stomach fails to close properly. The LES may fail to close because it is diseased or has atrophied. Alternatively, patients having cancer or a tumor in the esophagus may have the LES forced open by a stent so that food and liquids can be ingested. The reflux of stomach acids into the esophagus causes severe heartburn and may contribute to the onset of other diseases.

One method of relieving GERD is to place an anti-reflux stent into the entrance of the stomach. An anti-reflux stent is a device that has a one-way valve to allow food and liquid to enter the stomach but prevents liquids from passing back through the valve. Examples of anti-reflux stents can be found in J. Valbuena, "Palliation of Gastroesophageal Carcinoma with Endoscopic Insertion of a New Anti-reflux Prosthesis," Gastrointestinal Endoscopy, Vol. 30, No. 4, pp. 241-243 (August, 1994) and U.S. Pat. No. 6,302,917.

A conventional anti-reflux stent has a tubular sleeve that hangs into the stomach and a stent that surrounds a portion of the sleeve to provide a lumen through which food and liquids may pass.

In general it is desirable that an anti-reflux stent provide a smooth lumen opening into the stomach and an outer surface that will limit tissue growth into the stent such that it remains open and could be removed if desired. In addition, it is desirable that the valve characteristics that are provided by the sleeve can be easily selected during manufacture.

SUMMARY OF THE INVENTION

The present invention is an anti-reflux stent that is placed into the opening of a stomach by a physician. The anti-reflux stent includes an extended inner sleeve, a stent surrounding a portion of the inner sleeve, and a coating over the stent such that the stent is bonded to the inner sleeve. The distal end of the inner sleeve is flexible such that it compresses under normal gastric pressure in the stomach to prevent stomach contents from flowing back into the esophagus. However, under increased esophageal pressure and peristaltic action, food and liquid can pass through the sleeve in its collapsed state to enter the stomach.

In one embodiment of the invention, the inner sleeve has thickness and flexibility such that it inverts into the stent with sufficient gastric pressure. The proximal end of the stent may be coated to allow the stent to be removed or may be free of coating to aid in stent retention. The proximal end of the stent may be cylindrical or flared radially outward such that the stent can be embedded in or secured to an esophageal lining.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7A and 7B show one embodiment of a form that creates a valve within an anti-reflux stent in accordance with another embodiment of the present invention;

FIG. 11C shows an application device having a capture and displacement device turned with respect to FIG. 11a;

DETAILED DESCRIPTION OF THE PREFERRED EMBODIMENT

Figure 1:
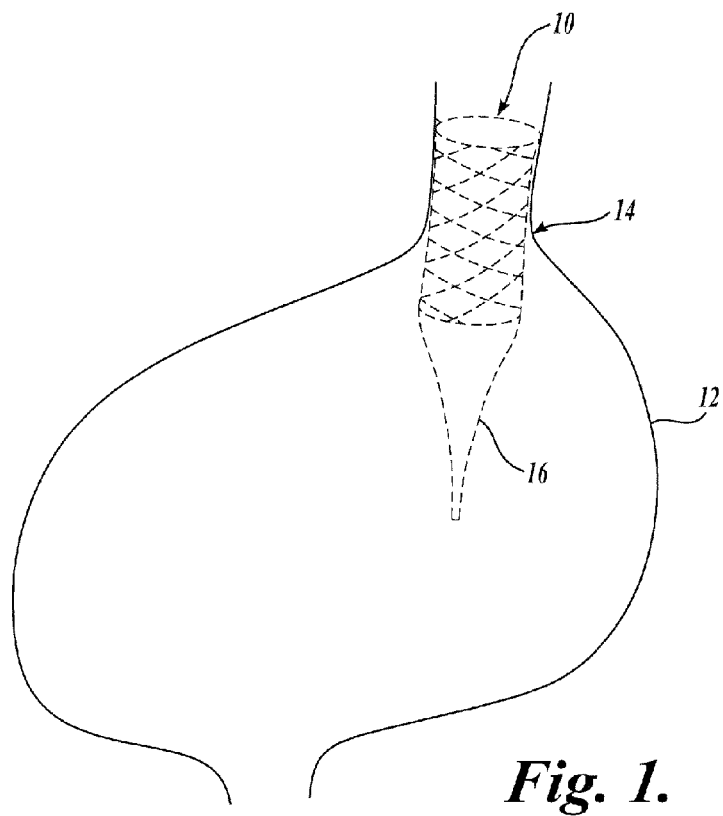
FIG. 1 illustrates a conventional anti-reflux esophageal stent in place in an opening of a stomach.

As indicated above, the present invention is an anti-reflux esophageal stent that allows a patient to ingest food or other liquid while preventing stomach acids from flowing back into the esophagus. FIG. 1 illustrates a conventional anti-reflux stent 10 that is placed at the entrance of a stomach 12 in the area of the lower esophageal sphincter (LES) 14. With the anti-reflux stent 10 in place, the proximal end of the stent forms a lumen into the opening of the stomach while the distal end acts to prevent the contents of the stomach 12 from entering the esophagus. The anti-reflux stent 10 comprises a flexible polymeric sleeve that collapses under the gastric pressure of the stomach 12 thereby forming a one-way valve. Food and liquid can pass in the distal direction through the collapsed sleeve but stomach acids do not flow in the proximal direction through the collapsed sleeve. However, the one-way valve can invert if the stomach pressure is sufficient to force the distal end 16 of the sleeve into the stent such as during vomiting or if the patient needs to belch. Details of the anti-reflux stent 10 are considered known to those of ordinary skill in the art and are for example disclosed in U.S. Pat. Nos. 6,302,917 and 6,162,244, which are herein incorporated by reference.

Figure 2:
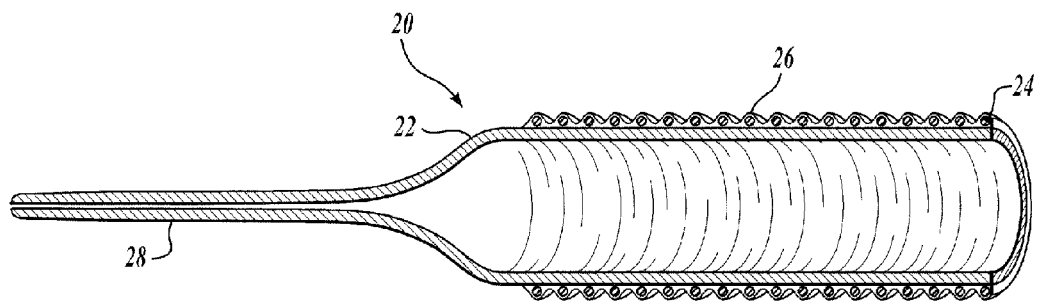
FIG. 2 is a cross-sectional view of an anti-reflux esophageal stent in a pressurized or closed position in accordance with one embodiment of the present invention.

FIG. 2 is a cross-section view of an anti-reflux esophageal stent in accordance with one embodiment of the present invention. The anti-reflux stent 20 has an inner sleeve 22, a stent 24 surrounding a portion of the inner sleeve 22 at the proximal end, and a coating 26 over the stent 24 that bonds the stent 24 to the inner sleeve 22. The inner sleeve 22 is preferably a polymeric tube that can be manufactured in a variety of manners including extrusion, molding, or forming the sleeve on a mandrel that is dipped into a polymeric solution. The materials and dimensions of the inner sleeve 22 are selected such that it will collapse in the area where it is not supported by the stent 24. Therefore, the sleeve 22 forms a one-way valve for passage of food or liquids into the stomach of a patient. Representative materials for the inner sleeve 22 include silicone, urethane or other flexible, bio-compatible materials.

In accordance with the present invention, the closure characteristics of the one-way valve can be tailored by the selection of the materials and/or dimensions of the inner sleeve. The sleeve may have different dimensions or thicknesses along its length. For example, the sleeve might be thicker in the portion that is covered by the stent and thinner at the portion that is not covered by the stent. In yet another embodiment, the inner sleeve may be made of different layers along its length by coating the inner sleeve with different materials such as silicone, polyurethane, or other surface enhancing, friction reducing or other modifying coatings. Furthermore, the sleeve could be extruded using two or more different materials in order to tailor the characteristics of the inner sleeve along its length.

The stent 24 bonded to the inner sleeve 22 may be a braided or knitted stent made from a variety of materials including polyester, nylon, stainless steel, Nitinol™ brand metal alloy, Kevlar™ or other materials that provide sufficient rigidity and strength. The stent is preferably self expanding but could be expandable by a balloon or other device. Examples of particular stents that could be used in an anti-reflux stent of the present invention are set forth in U.S. Pat. Nos. 4,954,126 and 4,655,771, which are herein incorporated by reference.

To bond the stent 24 to the inner sleeve 22, a coating 26 covers the stent 24. The coating covers the fibers that comprise the stent thereby sealing it to the inner sleeve 22. To obtain the best possible adhesion, it is believed that the coating 26 should be made of the same material as the inner sleeve 22. Therefore, if the inner sleeve 22 is made of a silicone material, then the coating 26 should be similarly made of a silicone material. Alternatively, if the inner tube 22 is made from a urethane material, then the coating 26 should also be made of a urethane-type material. While the use of similar materials is believed to be preferred, other materials may provide sufficient strength and bonding properties to coat the stent and adhere it to the outer surface of the inner sleeve 22. Various thicknesses of the outer coating can be made by varying the dipping rate or building up a coating as a number of different layers.

Figure 2A:
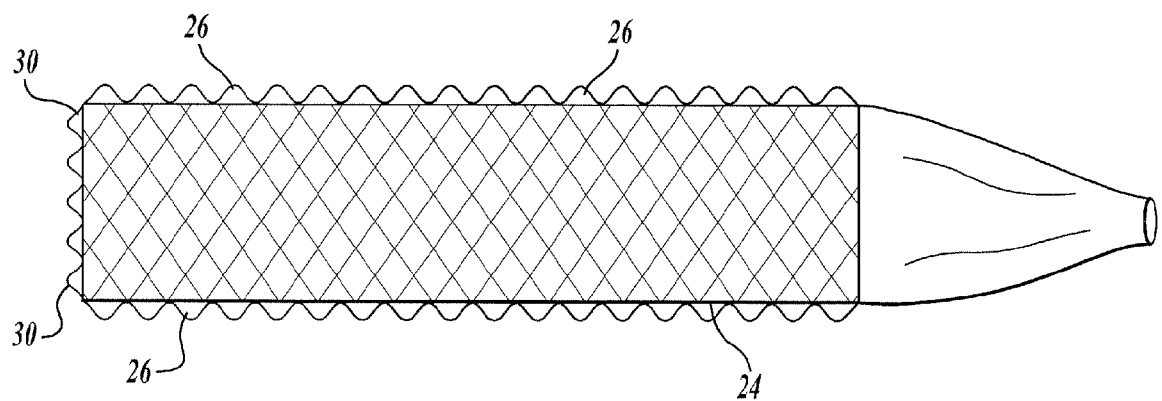
FIGS. 2A and 2B illustrate one technique for removing an anti-reflux stent in accordance with the present invention.

As shown in FIG. 2A, the majority of the stent 24 is covered by a coating 26. At the proximal end of the stent are a number of bare wire or thread loops 30 that allow the anti-reflux stent to be retrieved from the patient.

Figure 2B:
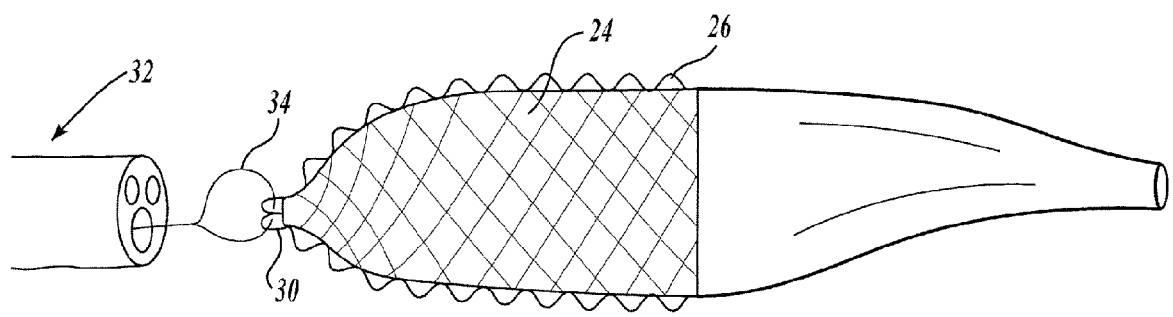

As shown in FIG. 2B, to retrieve the stent, a catheter 32 is inserted into the esophagus and a suture is passed through a lumen of the catheter and through a number of the loops 30 to cinch the proximal end of the stent closed. With the proximal end of the stent 24 cinched, its diameter is decreased and the endoscope and anti-reflux stent can be withdrawn from the patient's esophagus. Alternatively, the cinched anti-reflux stent may be fully or partially retracted into a retrieval tube prior to being withdrawn from the patient. The coating 26 over the stent 24 limits the ingrowth of tissue into the stent and may be lubricous to aid in its removal.

Figure 3:
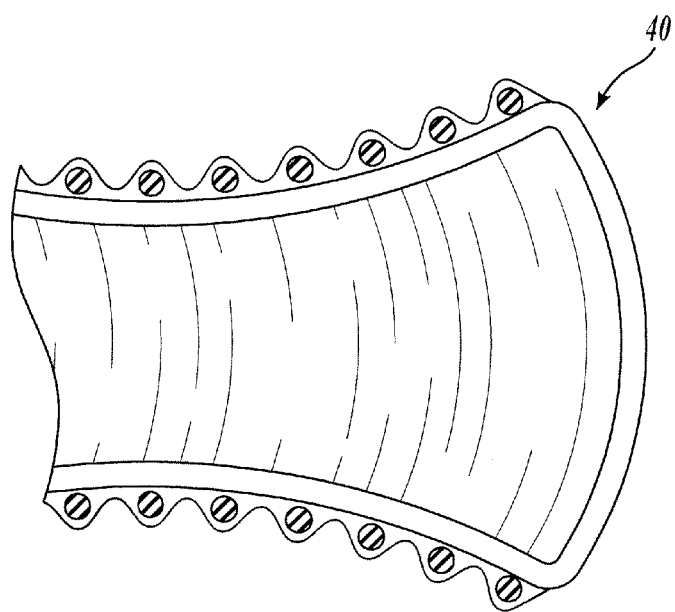
FIG. 3 illustrates the proximal end of an anti-reflux esophageal stent having a flared end.
Figure 4:
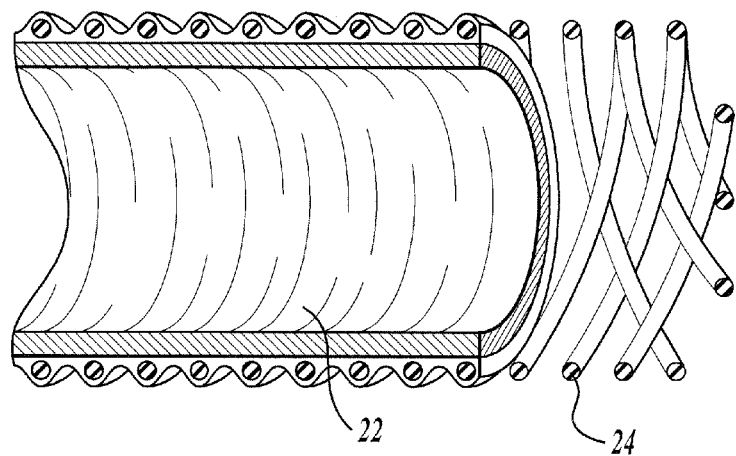
FIG. 4 illustrates an anti-reflux esophageal stent having a non-coated portion.

In the example shown in FIG. 2, the proximal end of the stent 24 has a generally cylindrical cross-section. However the diameter of the stent may vary along its length. For example, the proximal end of the stent may be flared radially outward such as that shown in FIG. 3. The flared proximal end 40 extends radially outward and may provide additional ability to hold the stent in place within the esophagus.

In yet another embodiment of the invention, the proximal end of the stent 24 does not overlap with the inner sleeve 22. That is, the proximal end of the stent 24 comprises a length of bare mesh. If the proximal end of the stent is not coated, tissue may grow into the interstitial spaces between the fibers or wires that comprise the stent thereby acting to secure the stent within the esophagus if desired. Alternatively, the physician can put a suture or other attachment mechanisms through the exposed portion of the stent to help maintain its position within the esophagus.

Figure 5:
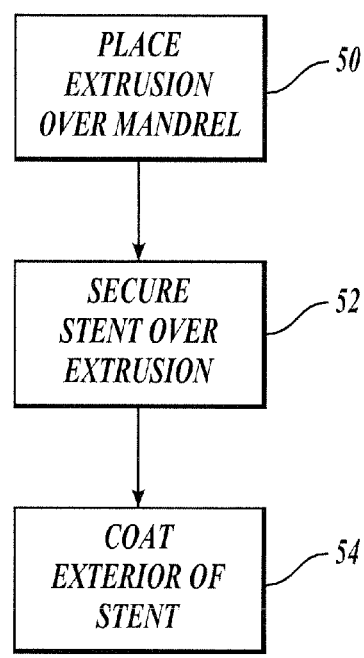
FIG. 5 is a flow chart showing a series of process steps used to make an anti-reflux esophageal stent in accordance with one embodiment of the invention.

FIG. 5 shows a series of process steps that can be used to manufacture an anti-reflux stent in accordance with one embodiment of the invention.

Beginning at a block 50, an extrusion that forms the inner sleeve is placed over a mandrel. At a block 52, a stent is placed over the proximal end of the extrusion. At a block 54, a coating is formed over the stent to secure it to the extruded inner sleeve. The coating may be formed by dipping the portion of the mandrel including the stent into a 2-part silicone bath or other coating material. Alternatively, the coating may be formed by spraying it or molding it over the stent. The mandrel is then removed from the inner diameter of the inner sleeve.

Figure 6:
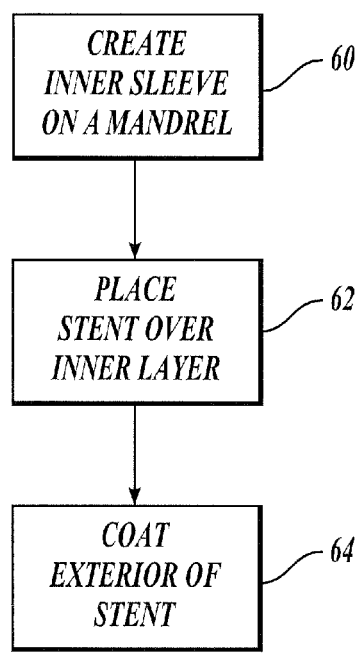
FIG. 6 is a flow chart showing a series of process steps used to make an anti-reflux esophageal stent in accordance with another embodiment of the present invention.

FIG. 6 shows an alternate series of process steps that can be used to make an anti-reflux stent in accordance with the present invention. Beginning at a block 60, an inner sleeve is created on a mandrel by dipping it in a material such as silicone or urethane bath. With the inner sleeve created on the mandrel, a stent is placed over the proximal end of the inner sleeve at a block 62. The exterior of the stent is then coated at a block 64 by dipping the mandrel including the stent into a material such as 2-part silicone or urethane bath. Alternatively, the coating can be applied by spraying or molding it over the stent. The mandrel is then removed from the inner sleeve.

In some embodiments, it may be desirable to add one or more valves to the anti-reflux stent. FIGS. 7A and 7B illustrates one method of creating a set of valves in an anti-reflux stent 70. The anti-reflux stent has an inner sleeve 72, a stent 74 covering a portion of the inner sleeve 72 and a coating 76 that bonds the stent 74 to the inner sleeve 72. A set of valve flaps 78*a*, 78*b*, 78*c* can be formed in an inner lumen of the inner sleeve 72 by inserting a form 79 into the inner lumen. The form has a divider 80 that divides the area of the lumen into sections. With the form 79 in place, the anti-reflux stent is dipped into a polymeric solution and the divider 80 creates valve flaps that are bonded to the interior lumen of the inner sleeve. The one or more valve flaps created when the form 79 is removed from the stent 70 further prevent the reflux of stomach acids into the esophagus. The valve flaps can be positioned anywhere along the length of the stent but may be advantageously positioned to align with an LES when the stent is installed.

Figure 8A:
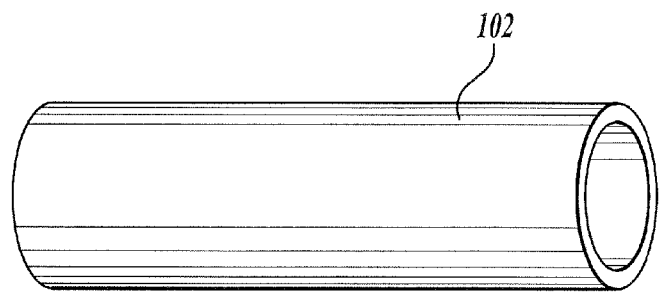
FIG. 8A shows a tube forming the basis of the stent.
Figure 8B:
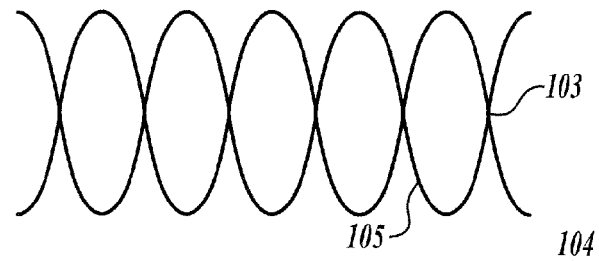
FIG. 8B shows a weave forming the basis of the stent.
Figure 8C:
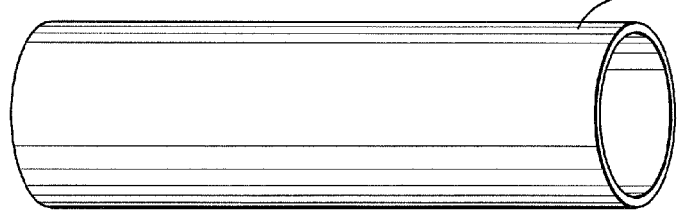
FIG. 8C shows a layer forming the basis of the stent in accordance with the invention.
Figure 8D:
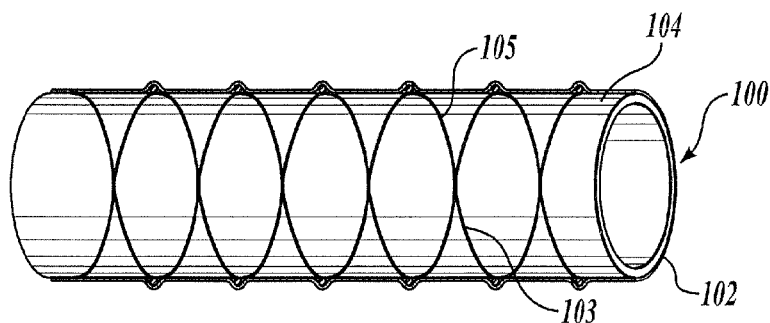
FIG. 8D is a schematic representation of the composition forming the stent in accordance with the invention comprising a tube, a weave and a coating.

FIGS. 8A-8D illustrate the construction of a stent 100 in accordance with the invention. The stent 100 consists essentially of an inner sleeve 102 (see FIG. 8A) made from elastic material, a tubular weave 103 tightly seating on the outer surface of the inner sleeve 102 (see FIG. 8B) and woven together from a plurality of filaments 105, as well as a coating 104 (FIG. 8C) introduced onto the outer surface of the inner sleeve 102. FIG. 8D shows the stent 100 in the constructed state. The inner sleeve 102 has a smooth inner surface and is strengthened through integration with the weaving 103 comprising the filaments 105, wherein the tubular weaving 103 and the inner sleeve 102 are joined by means of the coating 104. In accordance with FIG. 8D, the coating 104 is constructed in such a fashion that the prominent structure caused by the filaments 105 on the outer surface of the tube 102 projects through the coating 104 to lead to a structured outer surface of the coating 104.

Figure 9:
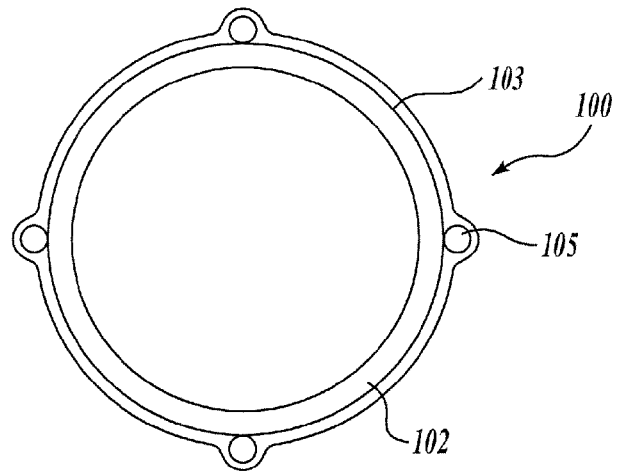
FIG. 9 shows a schematic cross section or end view of the stent of the invention in accordance with FIG. 8d.

FIG. 9 shows a schematic cross-section or end view of the stent in accordance with the invention. The inner sleeve 102 as well as the weave 103, comprising the filaments 105 and tightly seating on the outer surface of the inner sleeve 102, are bonded together by means of the relatively thin coating 104. In the embodiment in accordance with FIG. 9, the stent 100 has a structured outer surface dominated by the filaments 105 of rounded cross-section on the outer surface of the inner sleeve 102. The coating 104 is thereby sufficiently thin that the spaces between the filaments 105 are not completely filled up, wherein the structure dominated by the filaments 105 at the outer surface of the inner sleeve 102 is simply covered in a sealed fashion using the coating 104.

Figure 10A:
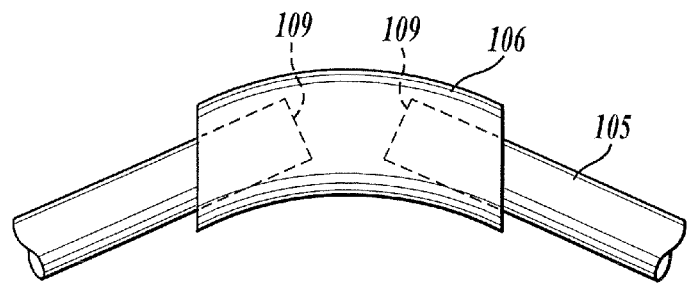
FIG. 10A shows an embodiment in accordance with the invention of capturing free filament ends using a cover cap.
Figure 10B:
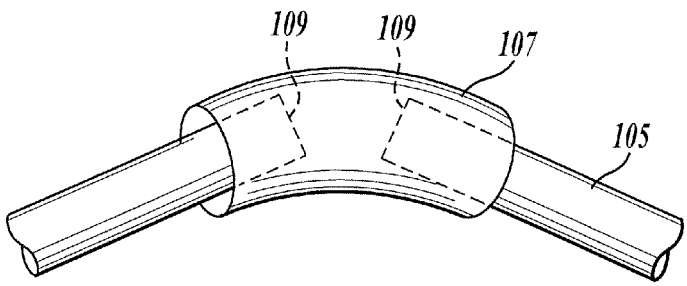
FIG. 10B shows an additional embodiment in accordance with the invention of captured filament ends using a filament tube.
Figure 10C:
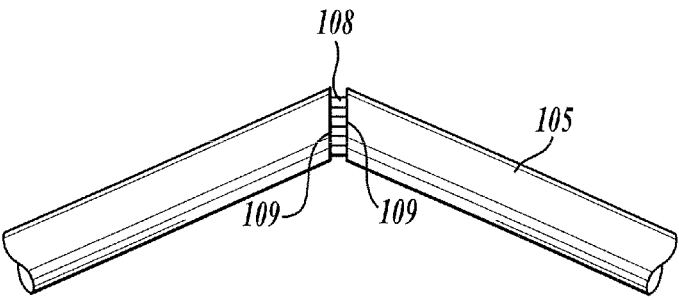
FIG. 10C shows an embodiment having welded filament ends.
Figure 10D:
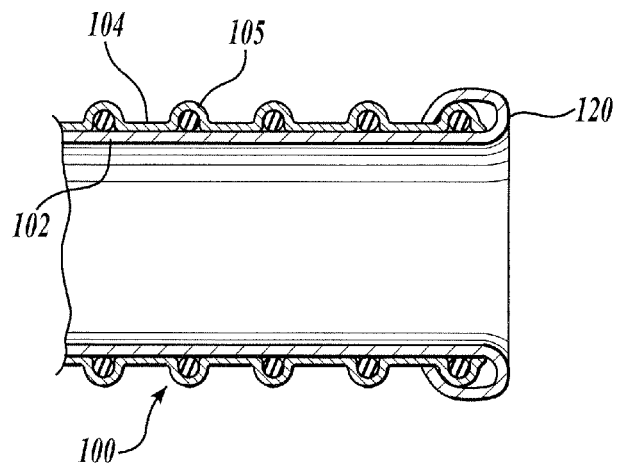
FIG. 10D shows a folding-over of the tube to effect capture of the filament ends.

The embodiments in accordance with FIGS. 10A-10D show different ways of holding the filament ends 109 together. In FIG. 10A, the ends 109 of the filaments 105 are connected to each other in a protected fashion using a cover cap 106. In accordance with FIG. 10B, the ends 109 of the filaments 105 are each connected to each other by means of a common filament tube 107. The free ends 109 of the filament 105 in accordance with FIG. 10C are held together and captured by means of a weldment 108. In accordance with FIG. 10D, it is also possible to capture the free ends of the filament 105 by means of a folding-over 120 of the inner sleeve 102.

Figure 11A:
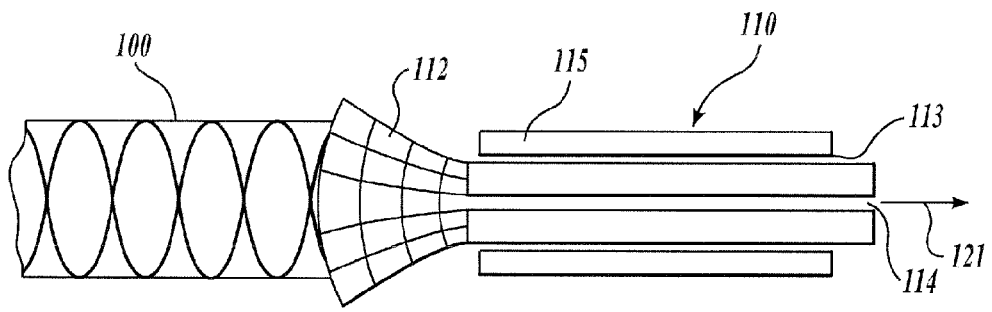
FIG. 11A shows an application device for placing the stent in accordance with the invention.
Figure 11B:
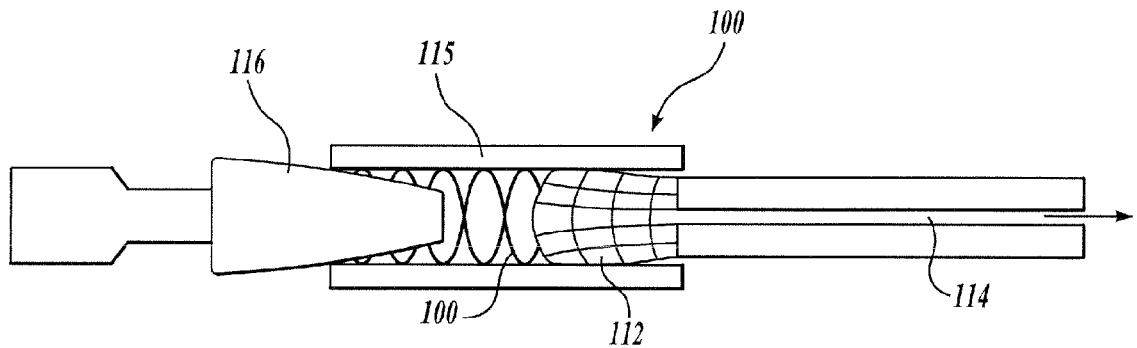
FIG. 11B shows an application device in accordance with FIG. 11a having an inserted stent and conical plug.

FIGS. 11A and 11B show an application device 110 which is suitable for introducing the stent 100 into a body cavity. The application device 110 in accordance with FIGS. 11A and 11B consists essentially of an outer application bushing 115 as well as an inner capture and displacement device 111. The inner capture and displacement device 111 has a spread-out capture device 112 at one end and is configured smoothly at the end opposite to the capture device 112. In addition, the capture and displacement device 111 has a lumen 114. In FIG. 11A, the stent 100 is pulled into the application device 110 in the direction of arrow 121 using the spread-out end of the capture device 112. The outer diameter of the capture and displacement device 111 is thereby dimensioned in such a fashion that it can be displaced within a lumen 113 of the application bushing 115. In accordance with FIG. 11C, a stent 100 which is already captured using the capture and displacement device 111 is displaced in the direction of arrow 122 out of the application bushing 115 and positioned within a body cavity.

Figure 11C:
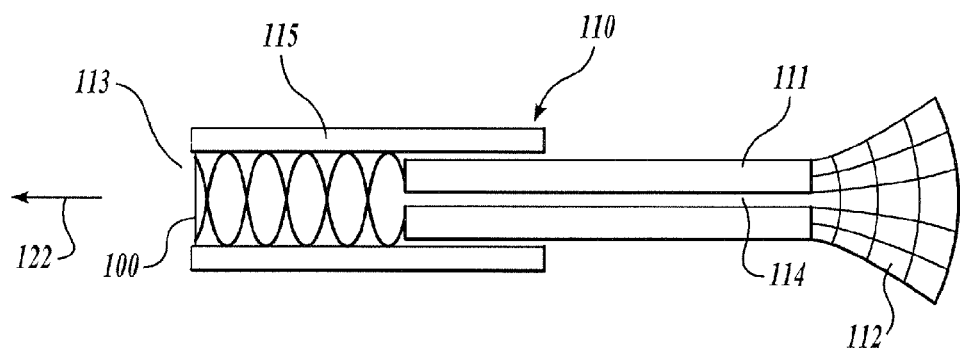

In order to utilize the application device in accordance with FIGS. 11A, 11B and 11C, the stent is initially pulled into the application bushing 115 in accordance with FIG. 11A by means of the spread-out end 112 of the capture and displacement device 111. After the stent 100 is completely within the application bushing 115 in accordance with FIG. 11B the stent 100 is positioned within the lumen 113 of the application bushing 115 by means of the conical plug 116. A guided motion of the capture device 112 in the direction of arrow 121 then frees the stent 100. The conical plug 116 is removed from the application bushing 115 and the capture and displacement device 111 is pulled out of the application bushing 115, turned around and once more inserted into the application bushing 115 at its other end (see FIG. 11C). Optical observation of the placing of the stent 100 is facilitated by an instrument which can be guided through a lumen 114. The application device 110 is subsequently placed and situated within the body cavity through displacement of the capture and displacement device 111.

Figure 12:
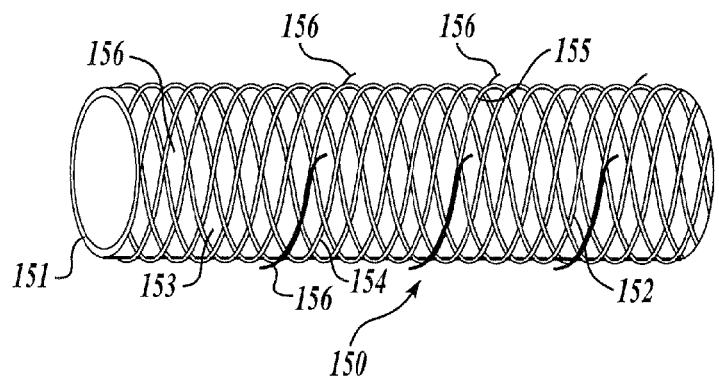
FIG. 12 shows a stent having raised portions on the outer peripheral surface formed by free ends of filament pieces.

FIG. 12 shows a stent 150 which is formed from a tube 151, a weave 152 and a coating 153. In addition to filament threads 154 from which the weave 152 is produced, a second filament thread 155 is adjacent to the threads 154 and is interrupted in sections, the free ends 156 of which protrude above the weave 152 and the coating 153. The free ends 156 build hooks for tissue adjacent to the outer surface of the stent.

Figure 13:
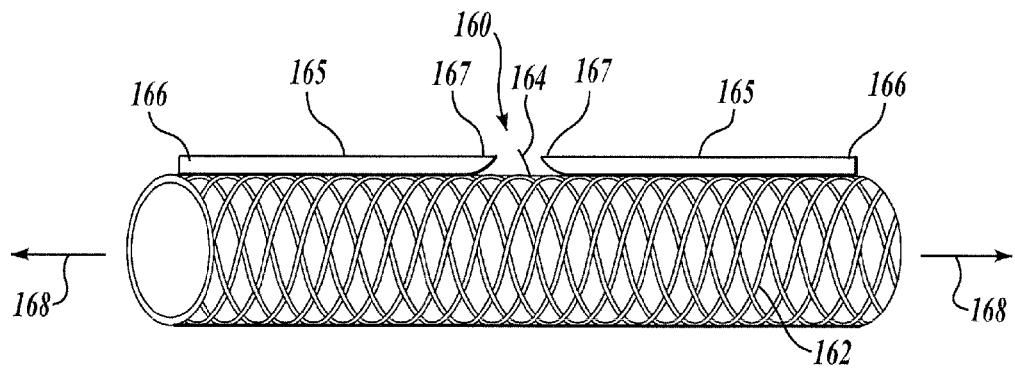
FIG. 13 shows a stent having anchors introduced on the outer surface in the extended state.

FIG. 13 shows another embodiment of a stent 160, in the elongated state, which has a weave 162. Anchors 165 are introduced on a flat section of outer surface 164 of the stent 166. Each anchor 165 is connected to the outer surface 164 of the stent 160 in a position-stable manner via first end 166. A second end 167 seats on the outer surface 164 of the stent 160. The stent 160 is elongated in the direction of arrow 168.

Figure 14:
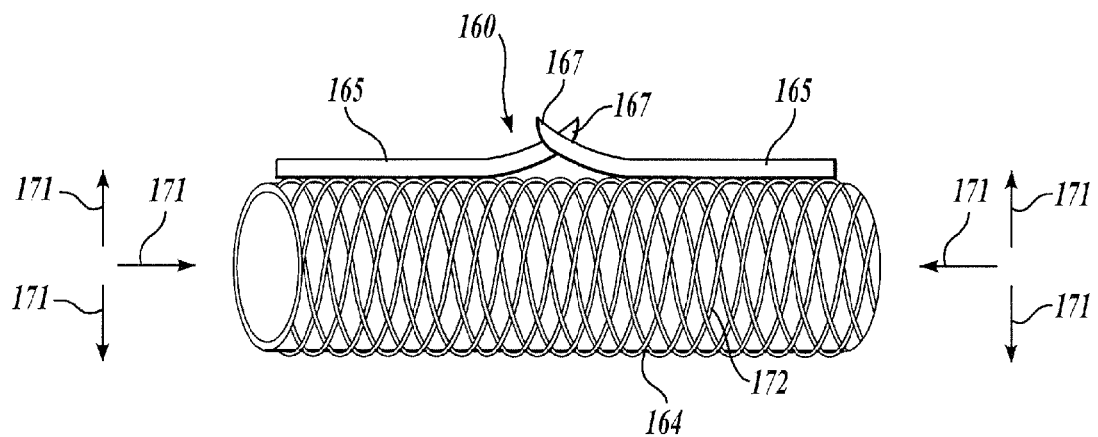
FIG. 14 shows a stent in accordance with FIG. 13 in an expanded state.

FIG. 14 shows the stent 160 of FIG. 13 in an expanded state. The stent 160 expands in the direction of arrow 171 so that an increased lumen 172 results. During expansion, the second ends 167 of the anchors 165 "stand up" and become separated from the outer surface 164. The second ends 167 facilitate the hooking or digging of the anchors 165 of the stent 160 into an adjacent surface.

Figure 15:
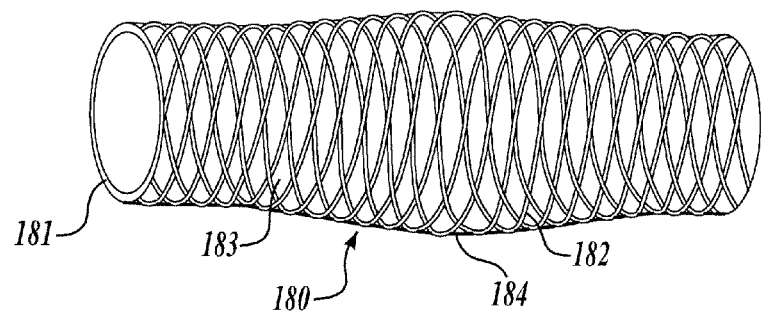
FIG. 15 shows a stent having differing surface contours in dependence on axial and radial directions.

FIG. 15 shows a stent 180 which likewise consists essentially of a tube 181, a weave 182 and a coating 183. The shape of the stent 180 differs in dependence on its axial and radial dimensions. The stent 180 assumes a distended shape 184 in an expanded state. The distended shape 184 is effected by weaving the weave 182 over a mould having this distended contour 184. The shape can be arbitrary and can be adjusted to the application. The distended shape 164 shown in FIG. 11 can be fashioned in a permanent manner using thermal shaping techniques.

Figure 16:
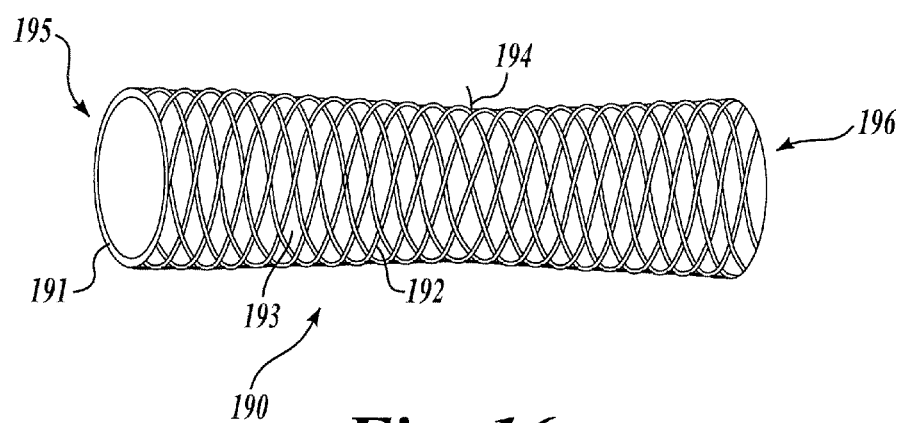
FIG. 16 shows a stent in an expanded state having widened lumens at each free end region.

FIG. 16 shows an additional embodiment of a stent 190, consisting essentially of a tube 191 supporting a weave 192 covered by a coating 193. As seen from the side, the outer shape of the stent 190 has a concave dependence 194 along its axial extent so that the stent 190 has free ends 195, 196 which define a wider lumen in both end regions of the stent 190. The free ends 195, 196 can be reinforced by means of ring structures on the outer surface of the stent 190. These ring structures can also be introduced on arbitrary sections of the stent at the outer surface thereof independent of the embodiment of FIG. 16.

The invention concerns a stent 100 for the bracing and/or holding-open of a body cavity having a tube 102 made from an elastic material, a tubular weave 113 comprising filaments 105 seating in close adjacency to the outer surface of the inner sleeve 102 as well as a coating 104 applied to the outer surface of the inner sleeve 102 which attaches the weave 103 to the outer surface of the inner sleeve 102. The coating 104 is adapted to have a structured outer surface dominated by the weave 103. The stent 100 in accordance with the invention can be produced economically with adjustable restoring forces and facilitates a secure placing within a body cavity. Means for preventing drifting within the body cavity can also be introduced onto the outer surface of the stent. In each of the FIGS. 8-16, an anti-reflux stent is created by lengthening the inner sleeve such that it is longer than the stent. With the sleeve sufficiently long, it will collapse in the stomach thereby forming a one-way valve to allow the passage of food and fluids into the stomach but prevent stomach acids from flowing back into the esophagus.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A coated stent, the coated stent having an outer surface and an inner surface, the coated stent comprising:
    a tubular inner sleeve, the inner sleeve having a proximal end and a distal end, the inner sleeve being made of a polymeric material;
    a stent covering at least a portion of the inner sleeve, the stent having a proximal end and a distal end, the proximal end of the stent being flared;
    a coating on the stent to bond the stent to the inner sleeve, the coating being a polymeric material that is the same as the polymeric material of the inner sleeve;
    a plurality of anchors engaged to the stent, the anchors extending radially outward from the stent;
    a valve positioned within the inner sleeve at a position that is covered by the stent having two or three valve flaps that close a lumen defined by the inner sleeve;
    wherein the inner sleeve has a length longer than the stent and the proximal end of the inner sleeve is distal to the proximal end of the stent;
    wherein the stent forms the outer and inner surfaces of a proximal end portion of the coated stent, the coating forms the outer surface of a middle portion of the coated stent, and the inner sleeve forms the outer surface of a distal portion of the coated stent and the inner surface of the middle and distal portions of the coated stent; and
    wherein the portion of the inner sleeve forming the distal portion of the coated stent has a flexibility that allows the inner sleeve to collapse and form a one-way valve.

2. The coated stent of claim 1, wherein the valve positioned within the inner sleeve includes only three valve flaps.

3. The coated stent of claim 1, wherein the inner sleeve is adapted to be inverted when a threshold amount of pressure is applied to the outside of the coated stent.

4. The coated stent of claim 1 where the coated stent comprises a weave, the weave having a plurality of first filaments and a plurality of second filaments where the plurality of second filaments are the plurality of anchors.

5. The coated stent of claim 4 where each of the plurality of second filaments comprise a first end and a second end and a body portion therebetween, the first end and the second end each defining a hook, the body portion immediately adjacent to a plurality of first filaments, each hook extending radially outward from the stent.

6. The coated stent of claim 1 where the stent comprises a weave, the weave having an outer surface, each of the plurality of anchors having a first end and a second end and a body portion therebetween, wherein the first end and the body portion are engaged to the outer surface of the weave, each of the plurality of anchors extending in a direction substantially parallel to a longitudinal axis of the stent.

7. The coated stent of claim 1, wherein the inner sleeve is made of silicone or urethane.

8. The coated stent of claim 1, wherein the inner sleeve has a thickness, the thickness varying along the length of the inner sleeve.

9. The coated stent of claim 8, wherein the at least a portion of the inner sleeve has a first thickness and the portion of the inner sleeve forming the distal portion of the coated stent has a second thickness, the second thickness being less than the first thickness.

10. The coated stent of claim 1, the inner sleeve having different layers along its length.

* * * * *